(12) United States Patent
Gelfand

(10) Patent No.: US 8,282,674 B2
(45) Date of Patent: Oct. 9, 2012

(54) CLAVICLE FIXATION

(75) Inventor: Jeffrey Gelfand, Severna Park, MD (US)

(73) Assignee: Suspension Orthopaedic Solutions, Inc., Arnold, MD (US)

( * ) Notice: Subject to any disclaimer, the term of this patent is extended or adjusted under 35 U.S.C. 154(b) by 1117 days.

(21) Appl. No.: 12/176,032

(22) Filed: Jul. 18, 2008

(65) Prior Publication Data

US 2010/0016899 A1    Jan. 21, 2010

(51) Int. Cl.
*A61B 17/80* (2006.01)
(52) U.S. Cl. ........................... 606/286; 606/280
(58) Field of Classification Search .............. 606/280, 606/71, 286
See application file for complete search history.

(56) References Cited

U.S. PATENT DOCUMENTS

| | | | |
|---|---|---|---|
| 4,655,203 A | 4/1987 | Tormala | |
| 5,190,545 A | 3/1993 | Corsi | |
| 5,275,602 A | 1/1994 | Shimizu et al. | |
| 5,350,383 A | 9/1994 | Schmieding | |
| 5,607,430 A | 3/1997 | Bailey | |
| 5,709,686 A | 1/1998 | Talos | |
| 5,928,267 A | 7/1999 | Bonutti | |
| 6,093,190 A | 7/2000 | Mattchen | |
| 6,514,274 B1 | 2/2003 | Boucher et al. | |
| 6,533,802 B2 | 3/2003 | Bojarski | |
| 6,592,609 B1 | 7/2003 | Bonutti | |
| 6,716,234 B2 | 4/2004 | Grafton | |
| 6,833,005 B1 | 12/2004 | Mantas | |
| 2001/0011172 A1 | 8/2001 | Orbay | |
| 2002/0019634 A1 | 2/2002 | Bonutti | |
| 2002/0062127 A1 | 5/2002 | Schumacher | |
| 2002/0065517 A1* | 5/2002 | Paul ................................ 606/69 |
| 2002/0077631 A1 | 6/2002 | Lubbers | |
| 2002/0143339 A1 | 10/2002 | Medoff | |
| 2002/0188297 A1 | 12/2002 | Dakin | |
| 2003/0050666 A1 | 3/2003 | Grafton | |

(Continued)

FOREIGN PATENT DOCUMENTS

EP    1 743 586    1/2007

(Continued)

OTHER PUBLICATIONS

Invitation to Pay Additional Fees and, Where Applicable, Protest Fee, dated Nov. 6, 2009 (from corresponding PCT Application No. PCT/US2009/048868).

(Continued)

*Primary Examiner* — Thomas Barrett
*Assistant Examiner* — Christine Nelson
(74) *Attorney, Agent, or Firm* — Womble Carlyle Sandridge & Rice LLP

(57) ABSTRACT

A substantially rigid plate is secured to a medial portion of a clavicle relative to a fracture in the clavicle. The plate is positioned so that it extends at least partially over a distal portion of the clavicle relative to the fracture. The plate has surfaces that define a first opening through which a suture can pass. A hole is formed in the clavicle. A washer may be positioned at a side of the plate opposite the clavicle. Alternatively, the plate may include suture holes or edge features for securing a suture. A suture is secured to the washer, to at least one suture hole or to at least one edge feature, and extends through the first opening, through the hole in the clavicle and is secured to the coracoid process.

15 Claims, 10 Drawing Sheets

U.S. PATENT DOCUMENTS

| | | |
|---|---|---|
| 2004/0059334 A1 | 3/2004 | Weaver |
| 2004/0102779 A1 | 5/2004 | Nesper |
| 2005/0010228 A1 | 1/2005 | Medoff |
| 2005/0085819 A1 | 4/2005 | Ellis |
| 2005/0216007 A1 | 9/2005 | Woll |
| 2005/0277929 A1 | 12/2005 | Raiszadeh |
| 2006/0004362 A1 | 1/2006 | Patterson |
| 2006/0058795 A1 | 3/2006 | Boyd |
| 2006/0106391 A1 | 5/2006 | Huebner |
| 2006/0122608 A1 | 6/2006 | Fallin |
| 2006/0122613 A1 | 6/2006 | Kirsch |
| 2006/0173458 A1 | 8/2006 | Forstein |
| 2006/0173465 A1 | 8/2006 | Meridew |
| 2006/0217722 A1 | 9/2006 | Dutoit |
| 2006/0229619 A1 | 10/2006 | Orbay |
| 2006/0235407 A1 | 10/2006 | Wang |
| 2006/0259039 A1 | 11/2006 | Pitkanen |
| 2006/0264950 A1 | 11/2006 | Nelson |
| 2007/0093835 A1 | 4/2007 | Orbay |
| 2007/0173834 A1 | 7/2007 | Thakkar |
| 2007/0173840 A1 | 7/2007 | Huebner |
| 2007/0179531 A1 | 8/2007 | Thornes |
| 2007/0185493 A1 | 8/2007 | Feibel |
| 2007/0225715 A1 | 9/2007 | Deffenbaugh |
| 2007/0233113 A1 | 10/2007 | Kaelblein |
| 2007/0250059 A1 | 10/2007 | Weisshaupt |
| 2007/0270853 A1 | 11/2007 | Leung |
| 2007/0293863 A1 | 12/2007 | Reimels |
| 2008/0004702 A1 | 1/2008 | Denoziere |
| 2008/0027440 A1 | 1/2008 | Marissen |
| 2008/0077133 A1 | 3/2008 | Schulze |
| 2008/0154260 A1 | 6/2008 | Hoof |
| 2008/0161805 A1 | 7/2008 | Saravia |
| 2008/0161861 A1 | 7/2008 | Huebner |
| 2008/0188936 A1 | 8/2008 | Ball |
| 2008/0195145 A1 | 8/2008 | Bonutti |
| 2008/0208262 A1 | 8/2008 | Butler |
| 2008/0221574 A1 | 9/2008 | Cavallazzi |
| 2008/0234676 A1 | 9/2008 | Schulze |
| 2008/0234679 A1 | 9/2008 | Sarin |
| 2008/0275508 A1 | 11/2008 | Haidukewych |

FOREIGN PATENT DOCUMENTS

| | | |
|---|---|---|
| GB | 2 257 913 | 1/1993 |
| WO | WO 86/07250 | 12/1986 |
| WO | WO 2007/014192 | 2/2007 |
| WO | WO 2007/063399 | 6/2007 |
| WO | WO 2008/045796 | 4/2008 |
| WO | WO 2008/096363 | 8/2008 |
| WO | WO 2008/113191 | 9/2008 |

OTHER PUBLICATIONS

Notification of Transmittal of the International Search Report and the Written Opinion of the International Searching Authority, dated Jan. 19, 2010 (from corresponding PCT Application No. PCT/US2009/048868).

"Arthroscopic Stabilization of Acute Acromioclavicular Joint Dislocation using the TightRope System", Arthrex publication, (2007).

Baleani, et al., "Surgical repair of the rotator cuff: a biomechanical evaluation of different tendon grasping and bone suture fixation techniques", Clinical Biomechanics, vol. 18, No. 8 pp. 721-729 (Oct. 2003).

Bradbury et al., "Clavicular nonunion: 31/32 healed after plate fixation and bone grafting", Acta orthopaedica Scandinavica, vol. 67, No. 4, pp. 367-370 (1996).

Braun et al., "The efficacy and integrity of shape memory alloy staples and bone anchors with ligament tethers in the fusionless treatment of experimental scoliosis", J Bone Joint, Surg Am. 2005 (9) pp. 2038-2051 (Sep. 2005).

Cicak et al., "Arthroscopic Transosseous Suture Anchor Technique for Rotator Cuff Repairs", Arthoscopy: The Journal of Arthroscopic & Related Surgery, vol. 22, No. 5, pp. 565.e1-565.e6 (May 2006).

Ebraheim et al., "Open Reduction and Internal Fixation with Bone Grafting of Clavicular Nonunion", Journal of Trauma-Injury Infection & Critical Care, 42(4) pp. 701-704 (Apr. 1997).

Flinkkilä, et al., "Surgical treatment of unstable fractures of the distal clavicle: a comparative study of Kirschner wire and clavicular hook plate fixation", Acta Orthop Scand, 73(1), pp. 50-53 (Jan. 2002).

Haidar, Saadallah George et al., "Hook Plate fixation for type II fractures of the lateral end of the clavicle", The Journal of Joint and Elbow Surgery, vol. 15, No. 4 (2006).

Khan et al., "Locking Compression Plate in Long Standing Clavicular Nonunions With Bone Stock", Journal of Trauma-Injury Infection & Critical Care, 64(2), pp. 439-441 (Feb. 2008).

Kim, et al., "The influence of Fixation Rigidity on Intervertebral Joints—An Experimental Comparison between a Rigid and a Flexible System", Journal of Korean Neurosurgical Society, pp. 364-369 (2005).

Lim, Andrew et al., "Traumatic retrosternal dislocation of the sternoclavicular joint of a young adult with generalised ligamentous laxity", Injury Extra, vol. 39, Issue 9, pp. 302-304 (Sep. 2008).

Lim, Yeow Wai et al., "Acromioclavicular Joint Reduction, Repair and Reconstruction Using Metallic Buttons—Early Results and Complications", Techniques in Shoulder & Elbow Surgery, vol. 8, Issue 4, pp. 213-221 (2007).

"Locking Clavicle Plate System", Acumed Publication, Effective: Jul. 2005.

Nho, et al., "Innovations in the management of displaced proximal humerus fractures", Journal of the American Academy of Orthopaedic Surgeons, vol. 15, No. 1, pp. 12-26 (Jan. 2007).

Rathjen, et al., "Stainless steel flexible intramedullary fixation of unstable femoral shaft fractures in children", Journal of pediatric orthopedics, vol. 27, No. 4, pp. 432-441 (2007).

J. Ryhänen, "Stabilization of acute, complete acromioclavicular joint dislocations with a new C hook implant", Journal of Shoulder and Elbow Surgery, vol. 12, Issue 5, pp. 442-445 (2003).

Sink, et al., "Complications of pediatric femur fractures treated with titanium elastic nails: A comparison of fracture types", Journal of pediatric orthopedics, vol. 25, No. 5, pp. 577-580 (2005).

Takahata, et al., "Comparison of Novel Ultra-high Molecular Weight Polyethylene Tape Versus Conventional Metal Wire for Sublaminar Segmental Fixation in the Treatment of Adolescent Idiopathic Scoliosis", Journal of Spinal Disorders & Techniques, 20(6): pp. 449-455 (Aug. 2007).

"What's New in Shoulder and Elbow Surgery", The Journal of Bone & Joint Surgery, vol. 90-A, No. 3, pp. 682-683 (2008).

"Invitation to Pay Additional Fees and Where Applicable, Protest Fee" in corresponding PCT Appln. No. PCT/US2009/048868, including Communication Relating to the Results of the Partial International Search, mailed Nov. 6, 2009.

* cited by examiner

CLAVICLE FIXATION

FIELD OF THE INVENTION

This invention relates to a system and method for clavicle fixation and, more particularly, a system and method for subcoracoid clavicle fixation to treat, for example, a fractured clavicle.

BACKGROUND

Distal clavicle fractures account for approximately 10% of all clavicle fractures. Many clavicular shaft fractures tend to heal without incident. However, complications often arise with respect to distal clavicle fractures. As a result, proper healing is less certain. Indeed, reported rates of nonunion in type II distal clavicle fractures have been between about 22% and 50%.

Numerous fixation methods have been proposed for the surgical management of distal clavicle fractures.

SUMMARY OF THE INVENTION

According to one aspect, a method of treating a fractured clavicle includes securing a substantially rigid plate to a medial portion of the clavicle relative to the fracture so that the secured plate extends at least partially over a distal portion of the clavicle relative to the fracture. The plate has surfaces that define a first opening through which a suture can pass. The method includes forming a hole in the clavicle, positioning a washer at a side of the plate opposite the clavicle and extending a suture through the washer, the first opening, and the hole in the clavicle and securing it to the coracoid process.

In a typical implementation, the suture is secured to the washer and tensioned at the washer to reduce the coraclavicular distance. Reducing the coraclavicular distance generally aligning the medial portion of the clavicle and the distal portion of the clavicle.

The first opening in the plate typically is elongated in a direction that generally follows the length of the clavicle. In certain embodiments, the hole in the clavicle is formed to be aligned with at least part of the first opening in the plate and to extend substantially toward the coracoid process.

According to some embodiments, the plate contains a recess at a side thereof opposite the clavicle and the recess is adapted to receive the washer. In such instances, the method includes positioning the washer substantially within the recess and engaging the suture to the washer. The washer may be adapted to fit snugly into the recess. The washer typically is substantially oblong and has one or more surfaces that define one or more holes that are distributed longitudinally across the washer.

In some implementations, securing the suture to the coracoid process includes wrapping the suture around the coracoid process. In some implementations, securing the suture to the coracoid process includes forming a hole in the coracoid process in substantial alignment with the hole in the clavicle, positioning an anchor coupled to the suture beneath the coracoid process with the suture passing through the hole in the coracoid process. The anchor may be substantially oblong and may be dimensioned so that in one orientation, it can pass through the hole, but in another orientation, it resists passing through the hole.

Certain embodiments of the method include securing the plate to the distal portion of the clavicle relative to the fracture.

In another aspect, a fixation system for a fractured clavicle includes a substantially rigid plate secured to a medial portion of the clavicle relative to the fracture. The secured plate extends at least partially over a distal portion of the clavicle relative to the fracture. The plate has one or more surfaces that define a first opening through which a suture can pass. A washer is positioned at a side of the plate opposite the clavicle. A suture is secured to the washer and extended through the first opening in the plate, through a hole in the clavicle and is secured to the coracoid process.

In some implementations, the suture is tensioned to reduce the distance between the coracoid process and the clavicle and to thereby bring the medial portion of the clavicle and the distal portion of the clavicle in substantial alignment with one another.

The first opening in the plate typically is oblong and extends in a longitudinal direction along the plate. The hole in the clavicle typically extends from a point along the first opening in the plate and extends substantially toward the coracoid process. In certain embodiments, the first opening in the plate defines a recess at a side of the plate opposite the clavicle. The recess is adapted to receive the washer. The fixation system of claim 16 wherein the washer fits substantially snugly in the recess. In some implementations, the washer can slide in a longitudinal direction within the recess.

In a typical implementation, the washer has one or more holes (e.g., two holes, three holes, four holes, five holes, six holes, seven holes or more), each of which is dimensioned to receive the suture. Typically, the fixation system also includes a hole in the coracoid process substantially aligned with the hole in the clavicle. The suture passes through the hole in the coracoid process. There typically is an anchor at an inferior side of the coracoid process and secured to the suture. The anchor may be oblong and typically is dimensioned to pass through the hole in the clavicle and through the hole in the coracoid process, and dimensioned to resist, once positioned beneath the coracoid process, returning through the hole in the coracoid process.

In some implementations, the suture is passed around the coracoid process.

Certain embodiments include a washer that is oblong and that includes a plurality of holes distributed longitudinally along the washer. The plate may optionally be further secured to the distal portion of the clavicle relative to the fracture. The plate is typically contoured to follow the shape of the clavicle. The plate may be secured to the clavicle using locking screws, non-locking screws or a combination of locking and non-locking screws.

In yet another aspect, a fractured clavicle fixation kit includes a substantially rigid plate contoured to be secured to a medial portion of the clavicle relative to the fracture and to extend at least partially over a distal portion of the clavicle relative to the fracture. The plate has surfaces that define: a first opening through which a suture can pass and a second opening to receive a fastening device. At least one fastening device is adapted to pass through the second opening in the plate to secure the plate to the medial portion of the clavicle. A washer is provided that can be positioned at a side of the plate opposite the clavicle. A suture is provided that is extendable between the washer and the coracoid process, through the first opening in the plate and that can be secured to the coracoid process.

Some embodiments include a substantially oblong anchor that can be coupled to the suture.

Another aspect includes a fixation system for a fractured clavicle that includes a substantially rigid plate with a series of screw holes and a series of suture holes. Each screw hole is adapted to receive a fastening device (e.g., a screw) that can fasten the plate to the fractured clavicle. The suture holes are smaller than the screw holes and closer together relative to one another than the screw holes are relative to one another. The substantially rigid plate is secured to a medial portion of the clavicle relative to the fracture and extends at least partially over a distal portion of the clavicle relative to the fracture. A suture is shown passing through one suture hole at an anterior side of the plate and through another suture hole at a posterior side of the plate. The suture extends between the suture holes and is tied above the upper surface of the plate. The suture extends through a hole in the clavicle and secured to the coracoid process.

In yet another aspect, a fixation system for a fractured clavicle includes a substantially rigid plate having edge features formed in a lateral edge thereof and screw holes distributed across the plate. Each screw hole is adapted to receive a fastening device that can fasten the plate to the fractured clavicle. The substantially rigid plate is secured to a medial portion of the clavicle relative to the fracture and extends at least partially over a distal portion of the clavicle relative to the fracture. A suture extends from an anterior side of the plate to a posterior side of the plate across the upper surface of the plate. The suture is prevented from sliding along the plate in a longitudinal direction by engagement with the edge features. The suture is extended through a hole in the clavicle and secured to the coracoid process.

In some implementations, one or more of the following advantages are present.

For example, a system and technique can be provided to effectively and securely hold a clavicle in place. This can aid in healing of distal fractures in the clavicle and other injuries, such as acromioclavicular (AC) joint dislocation.

The technique is relatively easy to implement. The resulting fixation arrangement is strong and durable and, therefore, less likely to fail under various stress conditions. The system provides for effective holding even when portions of the clavicle itself are severely compromised from a structural perspective.

The system can remain in place after the injury heals, thereby avoiding the need for intrusive procedures to remove hardware.

Other features and advantages will be apparent from the description and drawings, and from the claims.

DETAILED DESCRIPTION OF THE DRAWINGS

The present application is directed to a system and method for clavicle fixation. The system and method may be used to treat, for example, distal clavicle fractures.

In general, the method includes securing a substantially rigid plate to a medial portion of the clavicle relative to the fracture so that the secured plate extends at least partially over a distal portion of the clavicle relative to the fracture. The plate has surfaces that define a first opening through which a suture can pass. The method also includes forming a hole in the clavicle. A washer is positioned at a side of the plate opposite the clavicle (e.g., above the plate) and a suture is passed through the washer, through the first opening in the plate, through the hole in the clavicle and is secured to the coracoid process, which is inferior to the clavicle.

Figure 1:
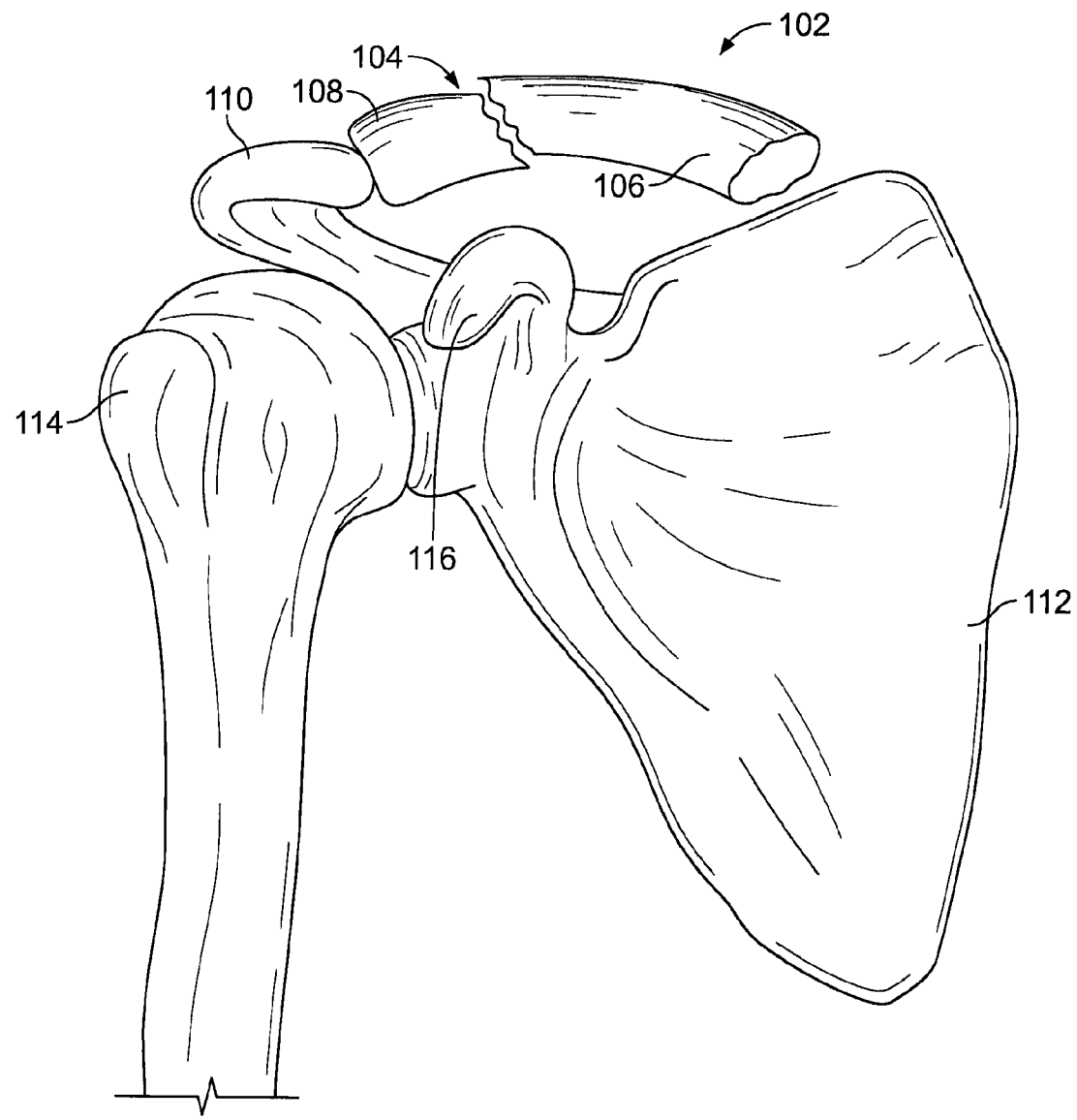
FIG. 1 is a partial perspective view of a person's shoulder area showing a fractured clavicle.

FIG. 1 is a partial perspective view of a person's shoulder area illustrating a clavicle 102 with a fracture 104 near a distal end thereof. The clavicle 102 has medial 106 and distal 108 portions relative to the fracture 104. The illustration also shows the acromion 110, the body of the scapula 112 and the humerus 114. The coracoid process 116 is a small hook-like structure that comes off the scapula 112. As shown in the illustrated implementation, the coracoid process 116 is located at least partially beneath part of the clavicle 102.

Figure 2:
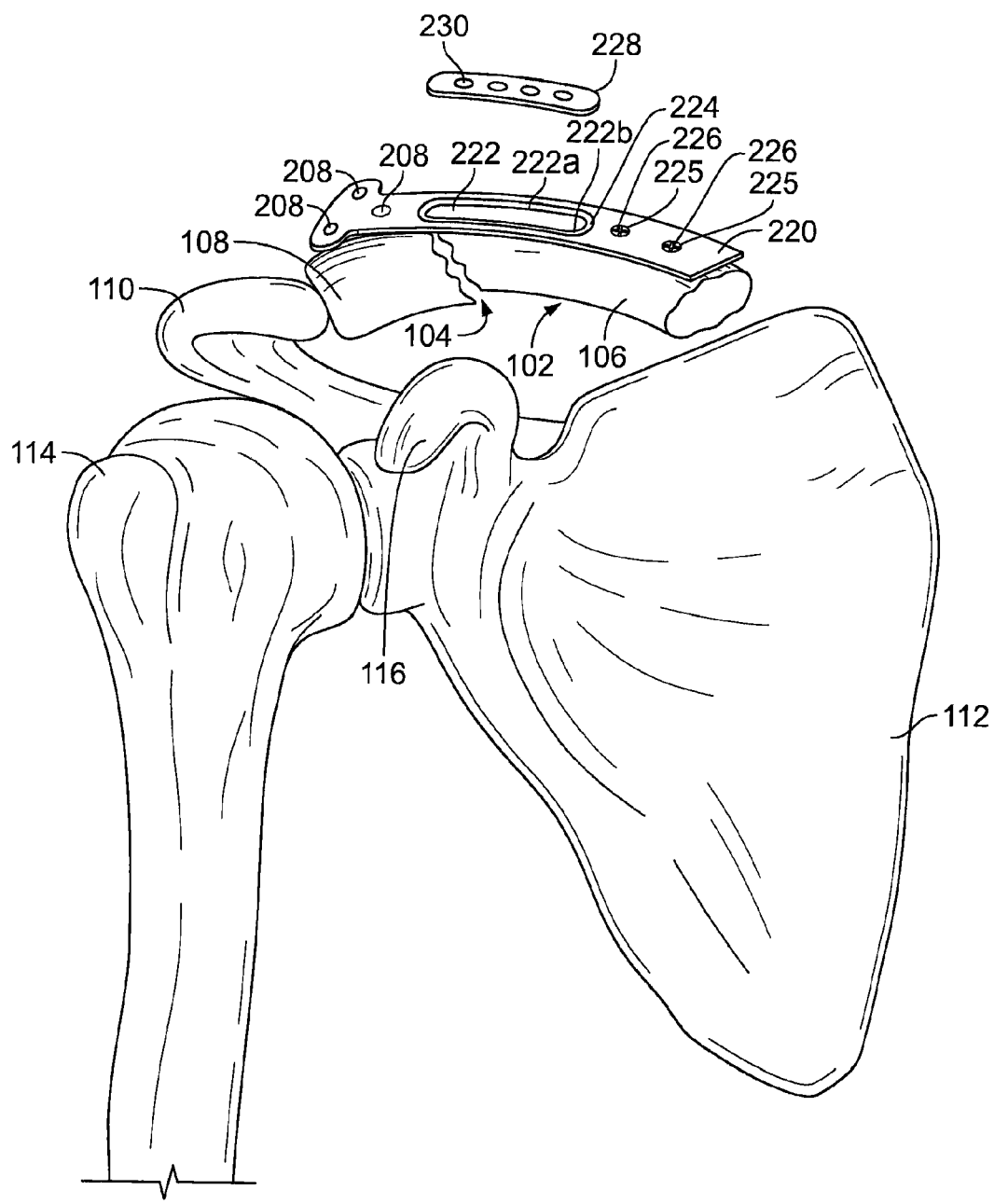
FIGS. 2-7 are various views of the person's shoulder area in FIG. 1 showing steps of one implementation of a treatment method for treating the fractured clavicle.

In FIG. 2, a substantially rigid plate 220 is shown secured to the medial portion 106 of the clavicle 102 relative to the fracture 104. The plate 220 is contoured to approximately follow the contours of an upper surface of a non-fractured clavicle. The illustrated plate 220 has surfaces that define a first opening 222, which is sized so that one or more sutures can pass through it, a pair of screw holes 225 at a medial end thereof and three screw holes 208 at a distal end thereof. The number of screw holes in the medial and distal ends of the plate 220 can vary. The distal end of the illustrated plate 220 is flared to accommodate a pair of side-by-side screw holes 208. The flare and side-by-side arrangement of screw holes 208 may facilitate secure fastening of the plate 220 to the distal portion 108 of the fractured clavicle 102. In contrast, the medial end of the illustrated plate 220 has no such flares.

The illustrated first opening 222 is substantially oblong having an elongated dimension extending in a direction that corresponds to the length of the plate. The first opening 222 has two sections—an upper, larger oblong section 222a that extends from the upper surface of the plate 220 down some distance to a shoulder 224, and a lower, smaller oblong section 222b that extends from the shoulder 224 to the bottom of the plate 220. The shoulder 224 has a substantially uniform width around a perimeter of the first opening 222.

In the illustrated implementation, the plate 220 is secured to the medial portion 106 of the clavicle 102 with a pair of screws 226, each of which passes through a respective one of the screw holes 225 at the medial end of the plate 220. Each screw 226 is threaded into the medial portion 106 of the clavicle 102, beneath the plate 220 and holds the plate 220 in place relative to the medial portion 106 of the clavicle 102. The screw holes 225 typically are far enough away from one another in the plate 220 so that the screws 226 in the screw holes 225 do not unduly compromise the integrity of the medial portion 106 of the clavicle 102.

As illustrated, the plate 220 is positioned so that it extends from the medial portion 106 of the clavicle 102, to which it is attached, over the fracture 104 and at least partially over the distal portion 108 of the clavicle 102 relative to the fracture 104. Typically, the plate 220 is positioned so that at least part of the lower, smaller section 222b of the first opening 222 is substantially directly superior to the coracoid process 116. Proper plate 220 position relative to the coracoid process may be confirmed fluoroscopically.

A washer 228 is positioned above the plate 220. The washer 228 has surfaces that define four holes 230 passing through the washer 228. The holes 230 are aligned with one another and distributed along a length of the washer 228. The washer 228 is substantially oblong and dimensioned to fit substantially snugly within the upper, larger oblong section 222a of the first opening 222 in the plate 220. Moreover, the illustrated washer 228 is dimensioned so that, when it is positioned within the upper, larger oblong section 222a of the first opening 222, it rests upon the shoulder 224 formed at the interface of the upper, larger oblong section 222a of the first opening 222 and the lower, smaller oblong section 222b of the first opening 222. The washer 228 also is dimensioned so that, when it is positioned within the upper, larger oblong section 222a of the first opening 222, its upper surface is approximately flush with the upper surface of the plate 220.

Figure 3:
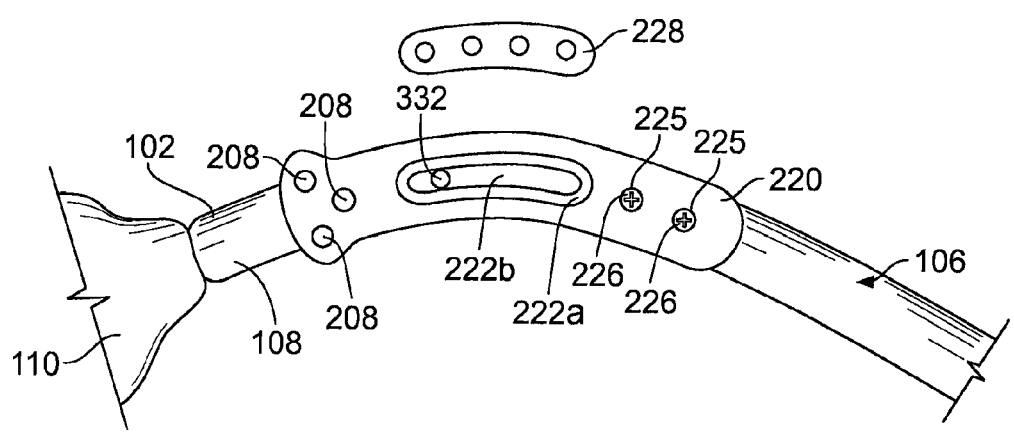

FIG. 3 is a partial plan view of the plate 220 of FIG. 2 shown secured to the medial portion 106 of the clavicle 102 relative to the fracture 104. The illustrated embodiment shows the position of a hole 332 that is formed (e.g., by drilling) in the clavicle 102 at a point along the first opening 222 in the plate 220. In a typical implementation, the hole 332 is formed so that it extends substantially toward the coracoid process 116 (see FIG. 2). The hole 332 may be formed using any number of known drilling or cutting techniques. In some implementations, only one hole (i.e., hole 332) is formed and that hole is in the clavicle 102. In some implementations, one hole (i.e., hole 332) is formed in the clavicle 102 and another hole (not shown in FIG. 3) is formed in the coracoid process 116 beneath the clavicle 102. In those implementations, the hole in the coracoid process 116 is preferably substantially aligned with the hole 332 in the clavicle 102.

Figure 4:
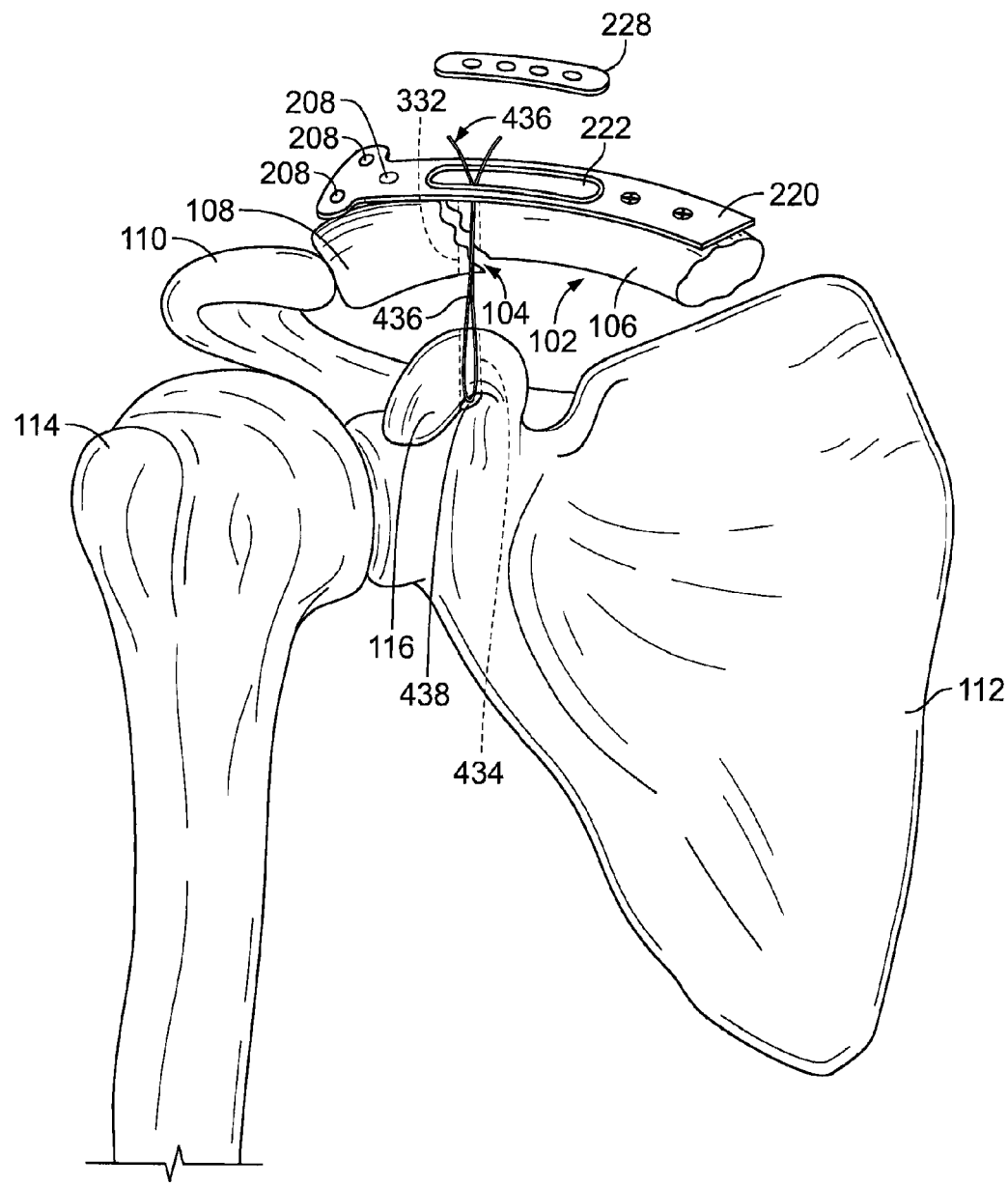

FIG. 4 shows the first hole (i.e., hole 332) in the clavicle 102 and a second hole 434 in the coracoid process 116 beneath the hole 332 in the clavicle 102 and substantially aligned with the hole 332 in the clavicle 102. In the illustrated implementation, the hole 332 in the clavicle 102 essentially passes through the fracture (i.e., through part of the medial portion 106 and through part of the distal portion 108 relative to the fracture 104). This illustrates that fixation can be effectively achieved even at points where the strength and structural integrity of the clavicle may be severely compromised (e.g., at the fracture itself). Nevertheless, the hole 332 in the clavicle 102 may be formed in the medial portion 106 of the clavicle only, the distal portion 108 of the clavicle only or, as shown, the medial 106 and distal 108 portions of the clavicle.

In the illustrated implementation, the hole 434 in the coracoid process 116 is substantially aligned with the hole 332 in the clavicle 102. In a typical implementation, the hole 434 in the coracoid process 116 has approximately the same diameter as the hole 332 in the clavicle 102. The hole 434 in the coracoid process 116 passes entirely through the coracoid process from an upper surface thereof to an exit surface beneath the coracoid process 116.

In some implementations, the hole 332 in the clavicle 102 may be sized to accommodate a drill guide sleeve (not shown). The drill guide sleeve may be passed through the hole 332 in the clavicle 102 and positioned to rest atop the coracoid process 116. With the drill guide sleeve so positioned, a drill can be passed through the drill guide sleeve and to the coracoid process 116. When used in this manner, the drill guide sleeve can provide control over creating the hole 434 in the coracoid process 116.

A suture 436 is extended through the first opening 222 in the plate 220, through the hole 332 in the clavicle 102 and the through the hole 434 in the coracoid process 116. The suture 436 is attached to an anchor 438 that is positioned beneath the coracoid process 116. The anchor 438 is substantially oblong and dimensioned so that it can be oriented to pass through the first opening 222 and through the holes 332, 434 and dimensioned so that it can be oriented, once in position beneath the coracoid process 116 that is too large to pass through at least the hole 434 in the coracoid process 116. Therefore, depending on the anchor's orientation relative to the first opening 222 and the holes 332, 434, it can either pass through or not pass through. As illustrated, the anchor 438 is oriented so that it cannot pass through the hole 434 and thereby is facilitating securing the suture 436 to the coracoid process 116.

In a typical implementation, the anchor 438 has one or more holes, through which the suture passes. The holes may be oblong, round, or have any shape (e.g., triangular, square or rectangular). The anchor 438 may be a metal material, such as titanium, titanium alloys or stainless steel, thermoplastics or other biocompatible and/or bioabsorbable materials. In a typical implementation, the anchor 438 has a length between about 9 mm and 20 mm, more preferably between about 12 mm and 15 mm, and a width less than about 1 mm narrower than the width of the drill holes through which the anchor is to pass through. In a typical implementation, the anchor may have a width of about 3.5 mm and a thickness of about 1.5 mm.

A variety of techniques may be used to create the holes 332, 434 and to position the suture 436 and anchor 438 therein. Such techniques may be, for example, open surgical techniques or arthroscopic techniques.

In an open surgical technique, for example, an incision may be made over the clavicle fracture 104 from approximately the acromioclavicular (A/C) joint to a distance of about 3-4 cm medial to the fracture 104. With the clavicle 102 so exposed, it may be possible to drill, using the first opening 222 in the plate as a guide, through the clavicle 102 and through the coracoid process 116. The direction and depth of drilling may be controlled and/or confirmed in a variety of ways, including, for example, by use of c-arm fluoroscopy. Once the holes are formed, the anchor 438, with the suture 436 attached may be fed through the hole 332 in the clavicle 102 and through the hole 434 in the coracoid process 116.

Another method of creating the holes and positioning the anchor 438 and suture 436 is an arthroscopic method using, for example, a cannulated drill and an Adapteur™ drill guide c-ring assembled with a coracoid drill stop attachment, available from Arthrex, Inc., of Florida. The technique is similar to what is described in U.S. Patent Application Publication No. 2007/0179531, the disclosure of which is hereby incorporated herein by reference in its entirety.

In general, the arthroscopic technique entails drilling a hole of about 4 mm through the clavicle and the coracoid using a C-Ring Adapteur guide and a cannulated drill and leaving the cannulated drill in the clavicle and the coracoid. With the cannulated drill so positioned, a suture passing wire is advanced through the cannulated drill and, subsequently, the drill is removed. Then, a pair of traction sutures from the anchor is passed through a wire loop formed by the suture passing wire. The suture passing wire is pulled on to retrieve the two traction sutures out of the anterior/inferior cannula. The anchor is advanced through the clavicle and the coracoid until it exits the coracoid base. Each of the traction sutures can be pulled on to flip the anchor onto the underside of the coracoid base, to thereby secure the anchor.

As illustrated, the free ends of the suture 436 are extended above the plate 220, passing through the oblong first opening 222. The free ends can be pulled in an upward direction so that the free ends pass through the first opening 222 directly above the hole 332 in the clavicle 102. Being able to pull substantially directly up on the suture relative to the hole 332 helps to facilitate reducing the clavicle to a position where it will be able to experience effective healing.

Figure 5:
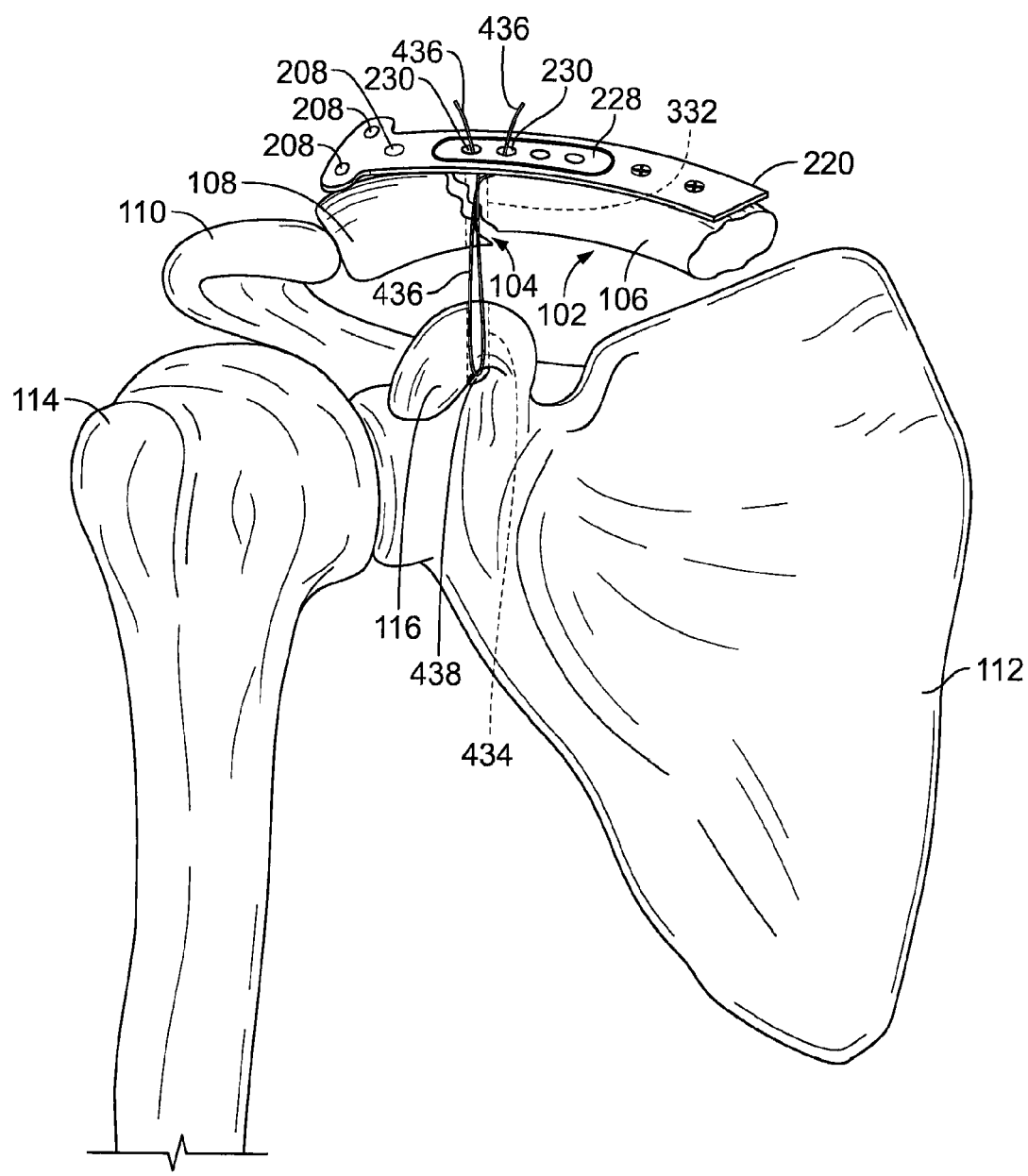

In FIG. 5, the suture and anchor 438 are affixed to the coracoid process 116 and the free ends of the suture 436 are extended above the plate 220, passing through the holes 230 in the washer 228 that are most directly above the hole 332 in the clavicle 102. The free ends may be placed through any holes in the washer 228 that are convenient. Generally, however, the holes 230 selected will be those that provide the most direct line of pull for the suture from the coracoid process 116.

The washer 228 is placed in the recessed portion of plate 220 (i.e., the larger, upper portion 222a of first opening 222 in the plate 220). In the illustrated implementation, the washer 228 fits substantially snugly in place in the recess. Moreover, the upper surface of the washer 228 is substantially flush with the upper surface of the plate 220.

Figure 6:
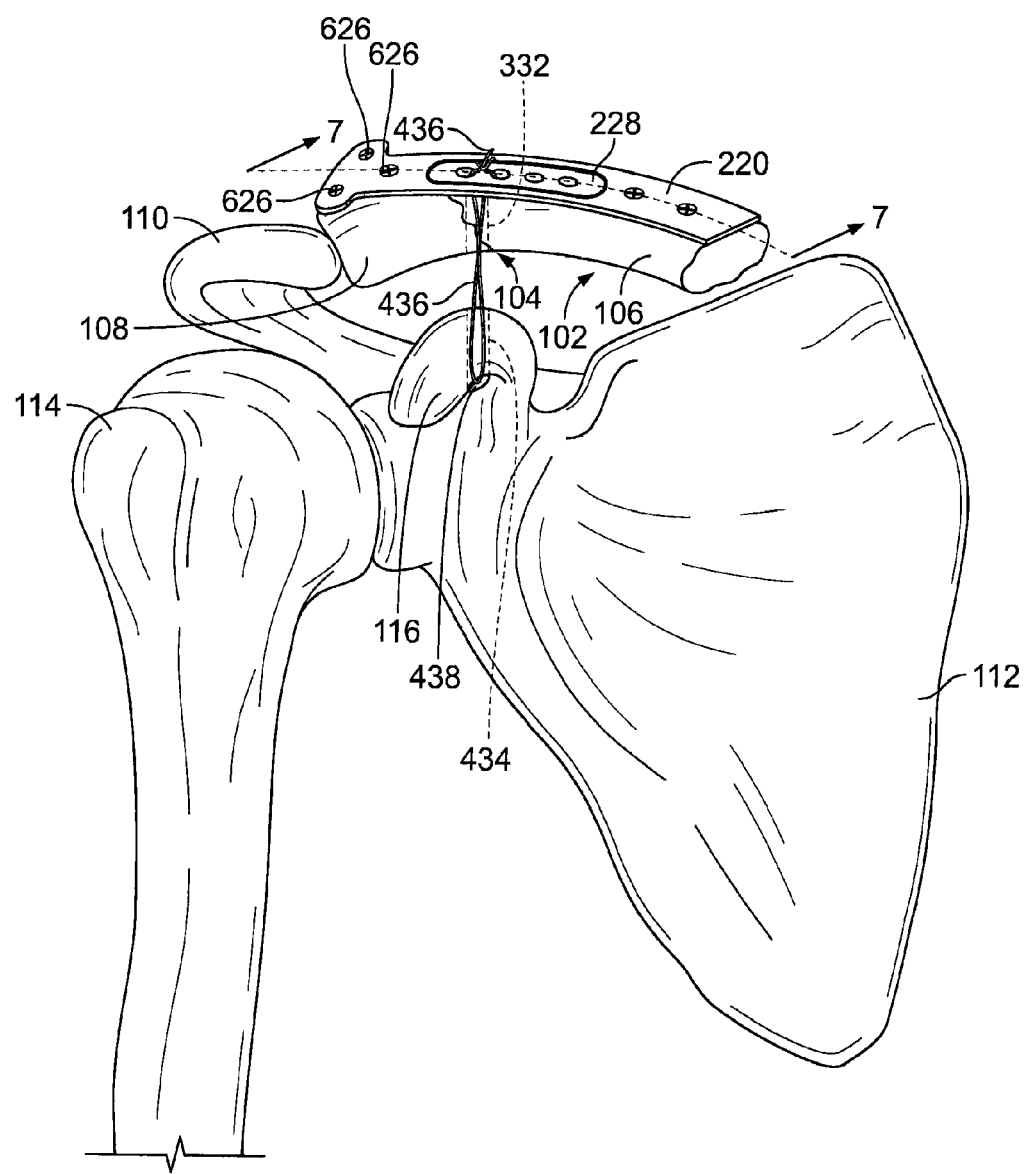

Referring now to FIG. 6, once the washer 228 is in place in the recess, the free ends of the suture 436 are tied to one another above the washer 228 and tightened a sufficient amount to reduce the clavicle and to restore approximately normal coracoclavicular distance. A variety of knots may be used to tie the free ends of the suture 436 together. In one implementation, for example, the free ends of the suture 436 are tied together using a surgeon's knot and two reverse half-hitches. Once the knot has been tied, the ends of the suture that extend beyond the knot may be cut.

One, two or three optional screws 626 may be introduced into any of the screw holes 208 at the distal end of the plate 220 to engage the distal portion 108 of the clavicle 102 relative to the fracture 104. In some implementations, using this screw 626 may help to hold the plate 220 in place above the clavicle 102. Moreover, using this screw 626 may help to further enhance alignment between the medial 106 and distal 108 portions of the fractured clavicle 102.

Figure 7:
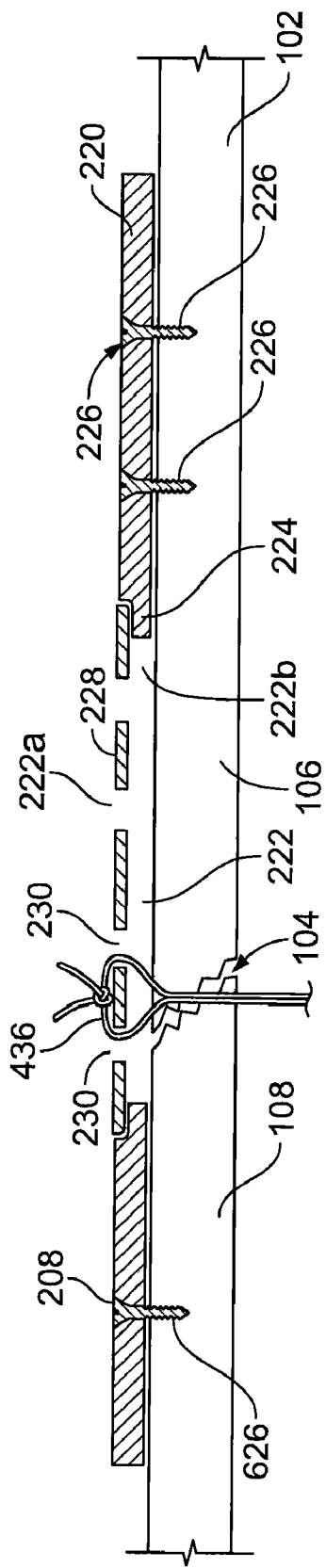

FIG. 7 is a cross-sectional view through the plate 220 and clavicle 102 of FIG. 6. In the illustrated implementation, the plate 220 is secured to the medial portion 106 of the clavicle 102 with two screws 226 and is secured to the distal portion 108 of the clavicle 102 with three screws 626. Typically, the two screws 226 secured to the medial portion 106 of the clavicle 102 are locking screws. The term "locking screw" may refer to a screw that has threads that engage the hole in the clavicle 102 and has threads that engage corresponding threads in the hole 225 in the plate 220. The three screws 626 secured to the distal portion 108 of the clavicle 102, however, may be either locking or non-locking screws or a combination thereof. The tops of the screws 226, 626 are substantially flush with the upper surface of the plate 220. The screws 226, 626 may extend part way through the clavicle 102 (as shown) or may extend completely through the clavicle.

The washer 228 is in place in the larger, upper portion of 222a of the first opening 222 in the plate 220. The washer 228 is positioned atop the shoulder 224 formed at the interface between the larger, upper portion 222a of the first opening 222 and the smaller, lower portion 222b of the first opening 222. The suture 436 is shown passing through two of the holes 230 in the washer 228. The ends of the suture 436 are tied together above the washer 228.

Figure 8:
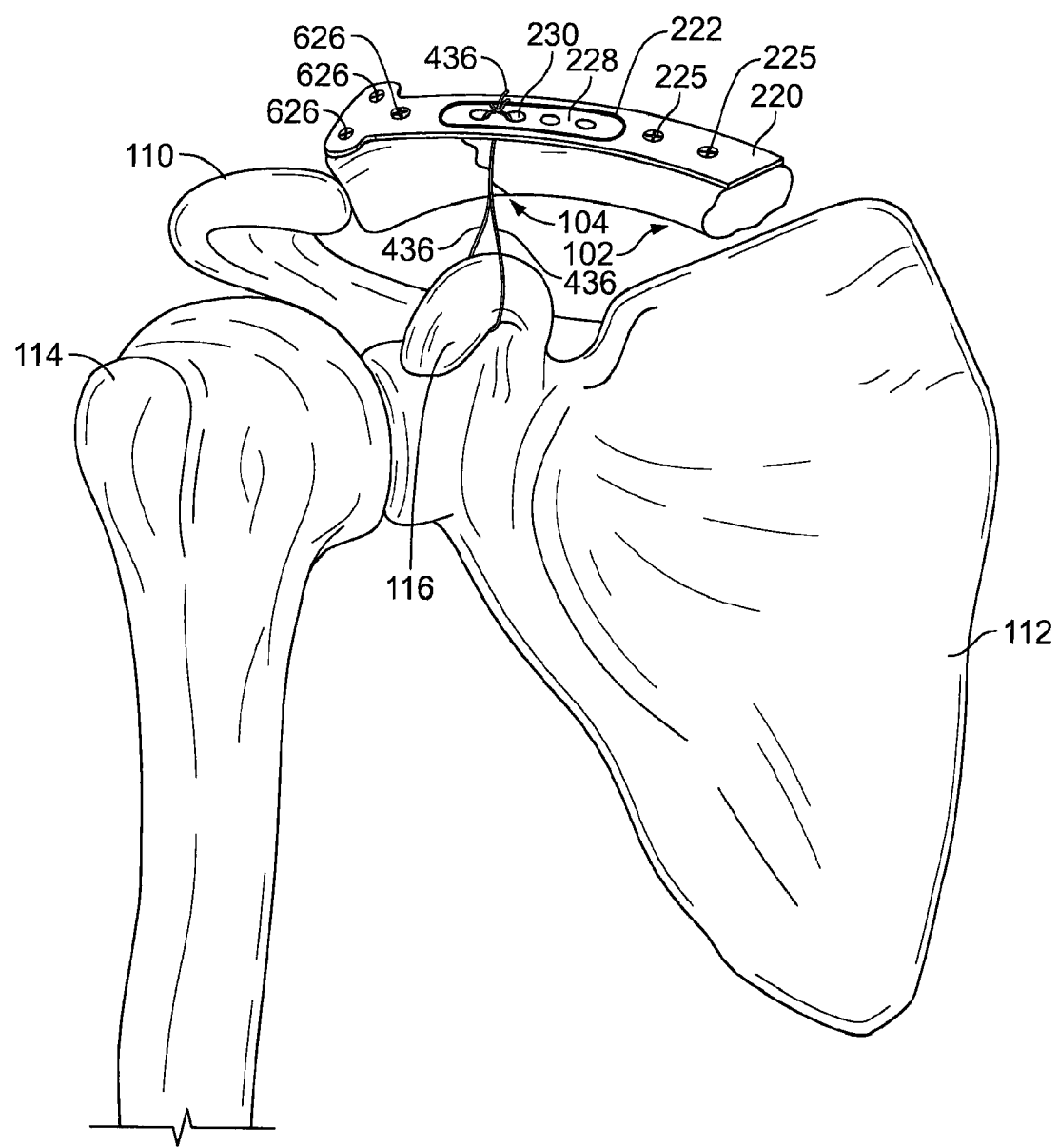
FIG. 8 is a partial perspective view of a person's shoulder area showing an alternative implementation of a clavicle fracture fixation system.

FIG. 8 shows an alternative clavicle fixation arrangement, in which subcoracoid fixation of the suture is achieved by extending the suture 436 around the coracoid process 116, instead of through a hole in the coracoid process 116. Otherwise, the arrangement is similar to that shown in FIG. 6, which is discussed above in detail. Typically, the arrangement of FIG. 8 may be implemented using an open (i.e., non-arthroscopic) surgical technique, in which the plate 220 is medially fixed to the clavicle with the first opening 222 placed substantially directly over the coracoid process. Once plate 220 is fixed medially, a hole is drilled through the clavicle 102 and a suture 436 is passed through the first opening 222 in the plate 220 and through the hole in the clavicle 102. Then, in a typical implementation, the anterior deltoid is subperiosteally elevated off the clavicle taking care to preserve thick fascial flaps granting exposure of coracoid process. Then, a curved suture passing device may be utilized to pass the suture underneath the base of the coracoid process under direct visualization. The end of the suture fed underneath the base of the coracoid process is then fed through the hole in the clavicle 102 and through the first opening 222 in the plate. The free ends of the suture are passed through holes 230 in the washer 228, which is positioned in the first opening 222. The free ends are then tied together and tightened an appropriate amount above the washer 228.

The sutures may be any type of suture suitable for use in connection with clavicle distal fracture fixation. In some implementations, more than one (e.g., two) strands may be used. Typically, the suture is a high strength, non-absorbable material. One example of a suitable suture material is disclosed in U.S. Pat. No. 6,716,234, assigned to Arthrex, Inc. of Naples Fla., the disclosure of which is hereby incorporated herein by reference in its entirety. More particularly, the suture may be made up of a cover and a core surrounded by the cover. Strands of ultrahigh molecular weight polyethylene and strands of polyester may be braided together to form the cover. The core may be formed of twisted UHMWPE. An example of a suitable suture is Ethibond™, available from Ethicon, Inc.

Figure 9:
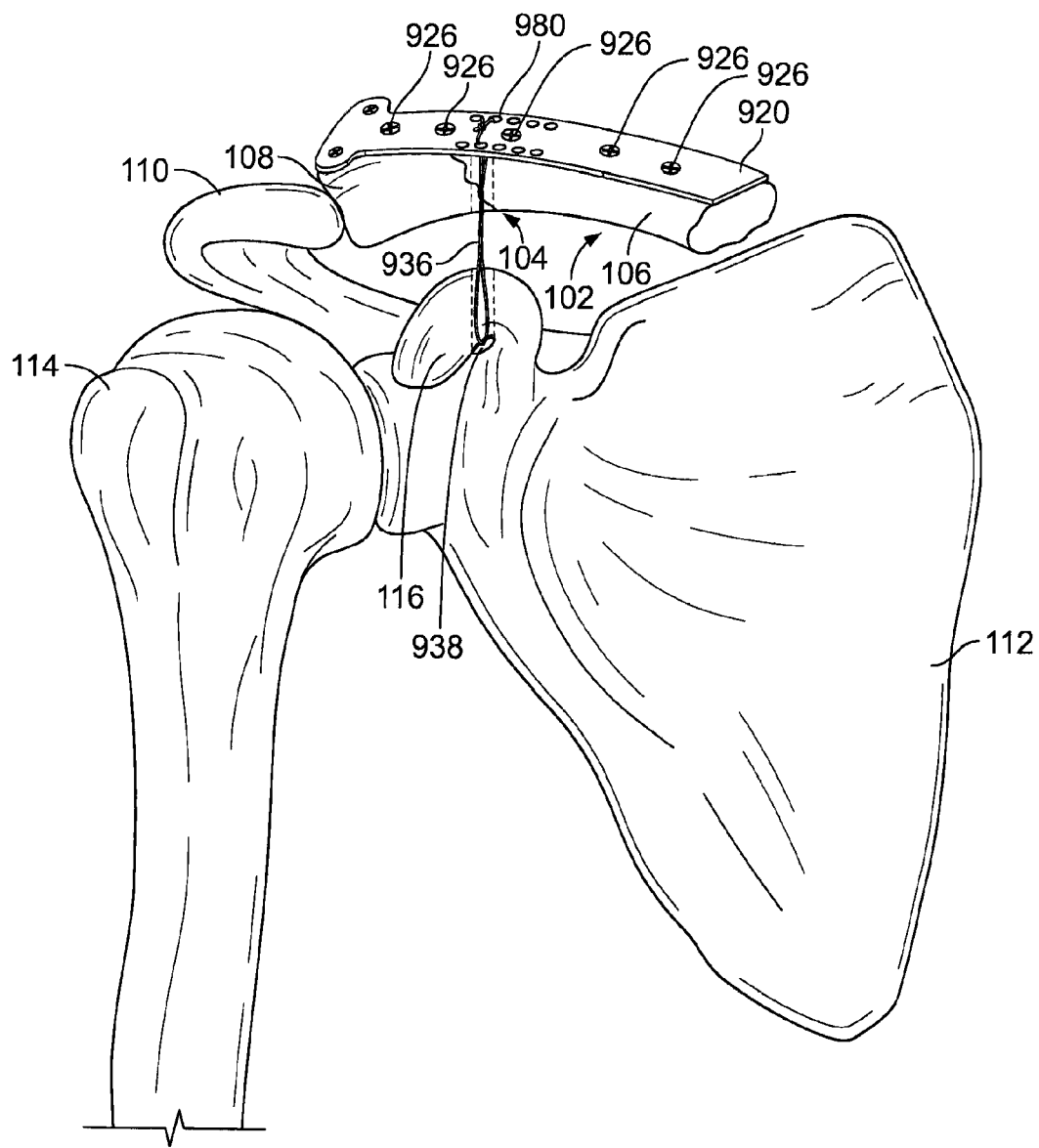
FIG. 9 is a partial perspective view of a person's shoulder area showing yet another alternative implementation of a clavicle fracture fixation system.

FIG. 9 is a partial perspective view showing an alternative implementation of a customized clavicle fixation plate 920 fastened to the fractured clavicle via fastening devices (e.g., screws 926) and fastened to the coracoid process 116 by a suture 936 and an anchor 938. Subject to a few exceptions, the illustrated assembly is similar to the assembly shown in FIG. 6. Most notably, the illustrated assembly does not include a washer above the plate 920. The suture 936 extends through a suture hole at an anterior side of the plate 920 and through a suture hole on a posterior side of the plate 920 is tied above the plate 920 between the holes.

The illustrated fixation plate 920 has a series of screw holes 908 distributed longitudinally along its centerline and a pair of screw holes 926 at a distal end of the plate 920 that are offset from its centerline. The screw holes 908 along the longitudinal centerline are approximately evenly spaced relative to one another. All of the screw holes 908 are sized to accommodate the passage of a fastening device (e.g., a screw) for fastening to the clavicle beneath the plate 920. In the illustrated implementation, seven screws 926 are provided—one in each hole—to secure the plate 920 to both the medial 106 and distal 108 portions of the fractured clavicle.

The illustrated plate 920 has two rows of suture holes 980, one row on either side of the screw holes 908. In each row, the suture holes 980 are arranged longitudinally along a portion of the plate. In the illustrated implementation, the suture holes are arranged along a middle portion of the plate 920 along its length. In each row, the suture holes 980 are approximately evenly spaced relative to one another.

The illustrated suture holes 980 are smaller than the screw holes 908 and are positioned closer to one another than the screw holes 908 are to one another. In some implementations, it is desirable that the suture holes 980 be as small as possible, but large enough at least to accommodate a suture (e.g., suture 936). It is also generally desirable that the suture holes be spaced as close together as possible.

In a typical implementation, the screw hole size is about 3.5 millimeters and the suture hole size is between 1 millimeter and 2 millimeters. The space between suture holes typically is approximately 2 millimeters. In one embodiment, the plate has 4 anterior and 4 posterior suture holes or edge feature "cut outs."

Since the illustrated suture holes 980 are offset from the clavicle plate's longitudinal centerline, the hole in the clavicle 102 beneath the plate 920 also may be offset relative to the clavicle plate's longitudinal centerline. Also, it is possible that two holes may be formed in clavicle, one for each leg of suture. Alternatively, the clavicle may have no holes and the suture may simply pass around the clavicle to the coracoid process.

Figure 10:
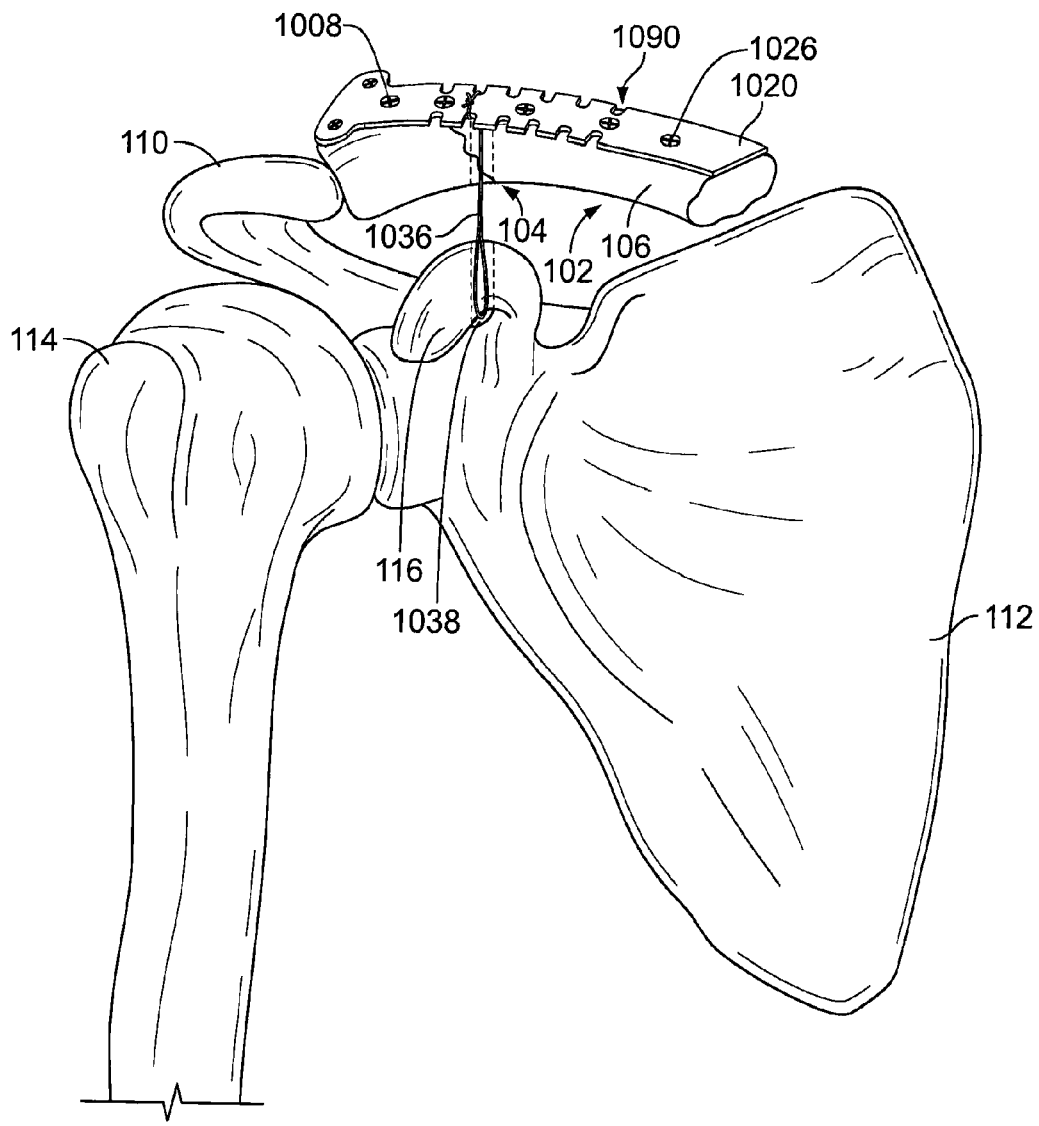
FIG. 10 is a partial perspective view of a person's shoulder area showing still another alternative implementation of a clavicle fracture fixation system.

FIG. 10 is a partial perspective view showing yet another alternative implementation of a customized clavicle fixation plate 1020 fastened to the fractured clavicle 102 via fastening devices (e.g., screws 1026) and fastened to the coracoid process 116 by a suture 1036 and an anchor 1038. Subject to a few exceptions, the illustrated assembly is similar to the assembly shown in FIG. 6. Most notably, the illustrated assembly does not include a washer. Accordingly, the suture 1036 is tied to the plate 1020 directly at the edge features 1090.

The illustrated fixation plate 1020 has a series of screw holes 1008 distributed longitudinally along its centerline and a pair of screw holes 1026 at a distal end of the plate 1020 that are offset from its centerline. The screw holes 1008 along the longitudinal centerline are approximately evenly spaced relative to one another. All of the screw holes 1008 are sized to accommodate the passage of a fastening device (e.g., a screw) for fastening to the clavicle 102 beneath the plate 1020. In the illustrated implementation, seven screws 1026 are provided—one in each hole—to secure the plate 1020 to both the medial 106 and distal 108 portions of the fractured clavicle 102.

In the illustrated implementation, the edge features 1090 include a series closely spaced-apart semi-circular etchings or cut outs in each of two opposite lateral edges of the plate 1020. The suture is tied to the plate 1090 directly at a longitudinal position on the plate where there are edge features 1090.

Since the illustrated edge features are at lateral edges of the fixation plate 1020 and, therefore, offset from the clavicle plate's longitudinal centerline, the hole in the clavicle 102 beneath the plate 920 also may be offset relative to the fixation plate's longitudinal centerline. Alternatively, there may be two holes—one at each side of the plate—in the clavicle. Alternatively, there may be no holes in the clavicle and the suture may be passed around the clavicle to the coracoid process.

A number of embodiments have been described. Nevertheless, it will be understood that various modifications may be made without departing from the spirit and scope of the invention. For example, the physical shapes and dimensions of the various system components (e.g., the plate, the anchor, the washer, and the suture) can vary considerably. For example, in some implementations, the washer may be substantially circular and the recess in the plate, in which the washer fits, may also be substantially circular. In such an implementation, there may be a row of holes in the washer that extends across a diameter of the circular washer. The washer can have any number of holes. Typically, the holes are formed in line with one another; however, they need not be aligned with one another.

The suture can pass through any two adjacent or non-adjacent holes in the washer and be tied above the washer. Typically, the specific holes that the suture passes through may be selected so that when the suture is tied and tightened above the washer, the clavicle is effectively reduced and the coraclavicular distance is corrected. Typically, the holes that are most directly in line with the holes in the clavicle and the coracoid process will be the holes that are used to tie the suture.

In some implementations, the hole for the suture in the clavicle could pass through the medial portion of the clavicle relative to the fracture only, the distal portion of the clavicle relative to the fracture only or both the medial and distal portions of the clavicle relative to the fracture.

The number and arrangement of screws used to secure the plate to the medial and distal portions of the clavicle relative to the fracture can be changed. Indeed, any number of screws may be used and the screws may be arranged in a variety of manners. The screws can be self-tapping or require that a hole be drilled and tapped. Moreover, other methods, such as the use of adhesives, of securing the plate to the clavicle may be used.

In some implementations, the medial end of the plate is flared to accommodate, for example, side-by-side screw hole placement. In some implementations, the distal end of the plate has substantially straight (i.e., not flared) sides with one or more holes disposed, for example, along a longitudinal axis of the plate. In some implementations, the plate does not include a recess for receiving the washer. In those instances, when installed, the washer may simply be positioned above the plate, but not in a recess. In some implementations, the recess is slightly larger than the washer to allow its position relative to the plate to be adjusted. This may be desirable to facilitate aligning two or more of the holes with the suture passing out of the hole in the clavicle.

In a plate that includes suture holes and/or edge features for securing a suture, the suture holes and/or edge features may or may not be evenly spaced, the suture holes and/or edge features may or may not extend along substantially the entire length of the plate. In some such implementations, the screw holes can be offset from the fixation plate's longitudinal centerline and the suture holes may be positioned along the longitudinal centerline. In some implementations, only one row of suture holes may be provided.

Edge features may have a variety of shapes, sizes, depths, etc. For example, instead of including a series of semi-circular etchings, they may include saw-tooth etchings, sinusoidal etchings, or castellations or any other shape suitable for securing a suture to. The edge features can be any size as well. In some implementations, the edge features may be provided along one edge of the plate only. The outer edges of the edge features may be wider than inner portions of the edge features. Such an arrangement may help keep the sutures secured to the edge features and prevent them from accidentally slipping off the edges of the edge features.

In an implementation that includes suture holes near a lateral edge of the plate, a suture may be secured to the plate by passing the suture through only one of the suture holes and around the lateral edge of the plate.

A variety of different plates may be used in connection with the foregoing techniques. Typically, the plates would be contoured to accommodate common anatomic variants of distal clavicles. In some implementations, the plate may have some degree of malleability.

The steps of the techniques described can be performed in a variety of different orders. In some instances, one or more of the steps described herein may be discarded completely.

Other implementations are within the scope of the claims.

What is claimed is:
1. A fixation system for a fractured clavicle, the fixation system comprising:

a substantially rigid plate contoured to follow the clavicle for securing to a medial portion of the clavicle relative to the fracture and to extend at least partially over a distal portion of the clavicle relative to the fracture when secured to the clavicle, the plate having one or more surfaces that define a substantially oblong first opening having a longitudinal dimension extending in a direction corresponding to the length of the plate and through which a suture can pass;

a washer that can be positioned at a side of the plate opposite the clavicle and configured to be slidably adjusted along the longitudinal dimension of the first opening;

a suture secured to the washer and extended through the first opening in the plate, configured to be passed through a hole in the clavicle and secured to the coracoid process.

2. The fixation system of claim 1 wherein the suture is configured so that upon tensioning the distance between the coracoid process and the clavicle is reduced to thereby bring the medial portion of the clavicle and the distal portion of the clavicle in substantial alignment with one another.

3. The fixation system of claim 1 wherein the first opening in the plate defines, at a side of the plate opposite the clavicle, a recess adapted to receive the washer.

4. The fixation system of claim 3 wherein the washer fits substantially snugly in the recess.

5. The fixation system of claim 1 wherein the washer has holes dimensioned to receive the suture.

6. The fixation system of claim 1 further comprising an anchor for positioning at an inferior side of the coracoid process and secured to the suture when the suture passes through a hole in the coracoid process.

7. The fixation system of claim 6 wherein the anchor is oblong and dimensioned to pass through the hole in the clavicle and through the hole in the coracoid process, and dimensioned to resist, once positioned beneath the coracoid process, returning through the hole in the coracoid process.

8. The fixation system of claim 1 wherein the suture is configured to pass around the coracoid process.

9. The fixation system of claim 1 wherein the washer is oblong and includes a plurality of holes distributed longitudinally along the washer.

10. The fixation system of claim 9, wherein sides of the washer are substantially parallel to the first opening in the plate.

11. The fixation system of claim 1 wherein the plate is contoured to be secured to the distal portion of the clavicle relative to the fracture.

12. The fixation system of claim 11, wherein a distal end of the plate is flared.

13. The fixation system of claim 1 further comprising locking screws.

14. A fractured clavicle fixation kit comprising:
a substantially rigid plate contoured to be secured to a medial portion of the clavicle relative to the fracture and to extend at least partially over a distal portion of the clavicle relative to the fracture, the plate having surfaces that define:
a substantially oblong first opening having a longitudinal dimension extending in a direction corresponding to the length of the plate and through which a suture can pass; and
a second opening to receive a fastening device;
at least one fastening device adapted to pass through the second opening in the plate to secure the plate to the medial portion of the clavicle;
a washer that can be positioned at a side of the plate opposite the clavicle and configured to be slidably adjusted within the longitudinal dimension of the first opening; and
a suture extendable between the washer and the coracoid process, through the first opening in the plate and through a hole formed in the clavicle.

15. The fractured clavicle fixation kit of claim 14 further comprising a substantially oblong anchor that can be coupled to the suture.

* * * * *